(12) United States Patent
Abrevaya et al.

(10) Patent No.: US 8,431,760 B2
(45) Date of Patent: *Apr. 30, 2013

(54) HYDROCARBON CONVERSION USING AN IMPROVED MOLECULAR SIEVE

(75) Inventors: Hayim Abrevaya, Kenilworth, IL (US);
Julio C. Marte, Carol Stream, IL (US);
John E. Bauer, LaGrange Park, IL (US)

(73) Assignee: UOP LLC, Des Plaines, IL (US)

( * ) Notice: Subject to any disclaimer, the term of this patent is extended or adjusted under 35 U.S.C. 154(b) by 846 days.

This patent is subject to a terminal disclaimer.

(21) Appl. No.: 12/365,584

(22) Filed: Feb. 4, 2009

(65) Prior Publication Data

US 2010/0152512 A1 Jun. 17, 2010

Related U.S. Application Data

(60) Provisional application No. 61/138,251, filed on Dec. 17, 2008.

(51) Int. Cl.
*C07C 5/22* (2006.01)
(52) U.S. Cl.
USPC ............ 585/477; 585/480; 585/481; 585/482
(58) Field of Classification Search ................... 585/477, 585/480, 481, 482
See application file for complete search history.

(56) References Cited

U.S. PATENT DOCUMENTS

| | | | | |
|---|---|---|---|---|
| 4,740,650 A | * | 4/1988 | Pellet et al. | 585/480 |
| 5,240,891 A | * | 8/1993 | Patton et al. | 502/66 |
| 5,276,236 A | * | 1/1994 | Patton et al. | 585/482 |
| 5,434,326 A | * | 7/1995 | Gajda et al. | 585/467 |
| 5,478,787 A | | 12/1995 | Dandekar et al. | |
| 6,660,896 B1 | | 12/2003 | Buchanan et al. | |
| 6,797,849 B2 | | 9/2004 | McMinn et al. | |
| 7,368,620 B2 | | 5/2008 | Zhou et al. | |
| 2007/0004947 A1 | * | 1/2007 | Zhou et al. | 585/481 |

FOREIGN PATENT DOCUMENTS

EP    0 158 349    11/1985

OTHER PUBLICATIONS

U.S. Appl. No. 12/365,518, filed Feb. 4, 2009, Abrevaya et al.
U.S. Appl. No. 12/365,536, filed Feb. 2, 2009, Abrevaya et al.
U.S. Appl. No. 12/365,584, filed Feb. 4, 2009, Abrevaya et al.

* cited by examiner

*Primary Examiner* — Elizabeth Wood
(74) *Attorney, Agent, or Firm* — Mark R Willis

(57) ABSTRACT

The present invention comprises a hydrocarbon-conversion process using an improved MgMxAPSO-31 molecular sieve which demonstrates a favorable combination of conversion and selectivity in aromatics conversion. The sieve comprises at least two divalent elements with narrow specific concentration limits in the framework structure having defined crystal characteristics. The element Mx may comprise one or more of manganese, cobalt, nickel, iron and zinc.

20 Claims, 21 Drawing Sheets

US 8,431,760 B2

HYDROCARBON CONVERSION USING AN IMPROVED MOLECULAR SIEVE

FIELD OF THE INVENTION

This invention relates to an improved molecular sieve and its use for the conversion of hydrocarbons. More specifically, the invention concerns a magnesium-containing non-zeolitic molecular sieve which has a narrowly defined composition and is particularly useful for isomerization.

GENERAL BACKGROUND AND KNOWN ART

Molecular sieves, most commonly zeolites, have a long history of use in catalysts for hydrocarbon conversion. More recently, a class of useful non-zeolitic ELAPSO molecular sieves containing framework tetrahedral units ($TO_2$) of aluminum ($AlO_2$), phosphorus ($PO_2$) and at least one additional element EL ($ELO_2$) have been disclosed for use in catalysts. In particular, such catalysts containing framework magnesium and designated MgAPSO-31 have demonstrated utility in the isomerization of $C_8$ aromatics.

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of products such as plasticizers, azo dyes, and wood preservers. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Paraxylene in particular is a major chemical intermediate with rapidly growing demand, but amounts to only 20-25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalyst composite and process which enhance conversion according to the latter approach, i.e., achieves ethylbenzene isomerization to xylenes with high conversion, is particularly advantageous.

SUMMARY OF THE INVENTION

A principal object of the present invention is to provide a novel molecular sieve which is useful for the conversion of hydrocarbons. More specifically, this invention is directed to a catalyst composite comprising a novel molecular sieve and a process for the isomerization of a mixture of xylenes and ethylbenzene resulting in improved yields and/or reduced processing costs.

This invention is based on the discovery that an ELAPSO molecular sieve containing at least two divalent EL elements within specific concentration limits in the framework structure with defined crystal characteristics provides a surprising effect in hydrocarbon-conversion activity.

Accordingly, a broad embodiment of the invention is a hydrocarbon-conversion process which comprises contacting a hydrocarbon feedstock in a conversion zone, at hydrocarbon-conversion conditions, with a catalyst comprising a MgMxAPSO molecular sieve wherein Mg and Mx represent elements in the crystalline framework structure, Mg represents magnesium and Mx represents one or more of the group consisting of manganese, cobalt, nickel, iron and zinc, and wherein the molar proportion of each of Mg and Mx in the crystalline framework structure on an anhydrous basis is between about 0.002 and about 0.01. The median crystal diameter is smaller than 2.5 micron and the median crystal length is smaller than 4 micron.

The mole fraction in the sieve framework of magnesium preferably is between about 0.003 and 0.008 and the mole fraction of the second element Mx preferably is between about 0.002 and 0.008.

A more specific embodiment is a hydrocarbon-conversion process which comprises contacting a hydrocarbon feedstock in a conversion zone, at hydrocarbon-conversion conditions, with a catalyst composite comprising a MgMxAPSO molecular sieve wherein Mg and Mx represent elements in the crystalline framework structure, Mg represents magnesium and Mx represents one or more of the group consisting of manganese, cobalt, nickel, iron and zinc, and wherein the molar proportion of each of Mg and Mx in the crystalline framework structure on an anhydrous basis is between about 0.002 and about 0.01. The median crystal diameter is smaller than 2.5 micron and the median crystal length is smaller than 4 micron. Also present is from about 0.1 to 5 mass % of a platinum-group metal component and an inorganic-oxide matrix.

A yet more specific embodiment is an isomerization process which comprises the steps of contacting a non-equilibrium feed mixture of xylenes and ethylbenzene in a first isomerization zone, at first isomerization conditions, with a first isomerization catalyst comprising at least one zeolitic aluminosilicate and an inorganic-oxide binder, to obtain an intermediate stream; and contacting the intermediate stream in a second isomerization zone, at second isomerization conditions, with a second isomerization catalyst comprising a MgMxAPSO molecular sieve wherein Mg and Mx represent elements in the crystalline framework structure, Mg represents magnesium and Mx represents one or more of the group consisting of manganese, cobalt, nickel, iron and zinc, and wherein the molar proportion of each of Mg and Mx in the crystalline framework structure on an anhydrous basis is less than about 0.01 mol fraction, a platinum-group metal component, and an inorganic-oxide matrix, to obtain a product comprising $C_8$ aromatics having an increased content of para-xylene.

These as well as other objects and embodiments will become evident from the following detailed description of the invention.

DETAILED DESCRIPTION OF THE INVENTION

Figure 1:
FIG. 1 is an SEM micrograph of catalyst sample 2A.
Figure 2:
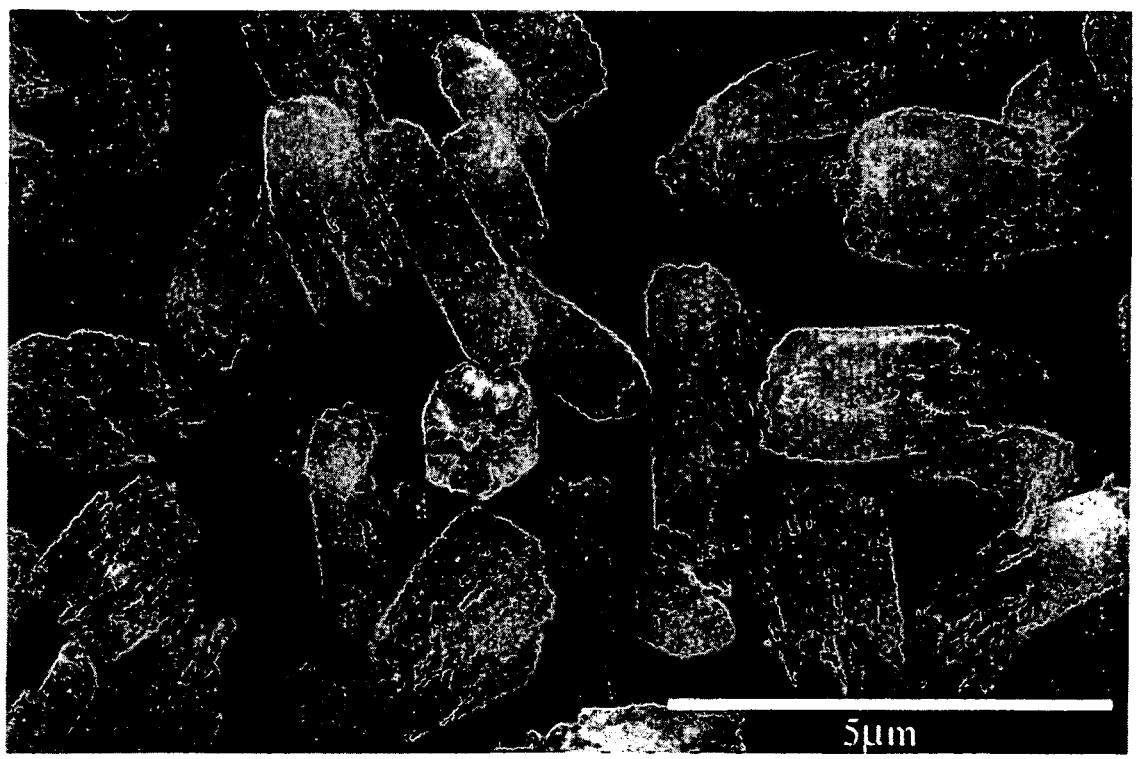
FIG. 2 is an SEM micrograph of catalyst sample 2B.
Figure 3:
FIG. 3 is an SEM micrograph of catalyst sample 2C.
Figure 4:
FIG. 4 is an SEM micrograph of catalyst sample 2D.
Figure 5:
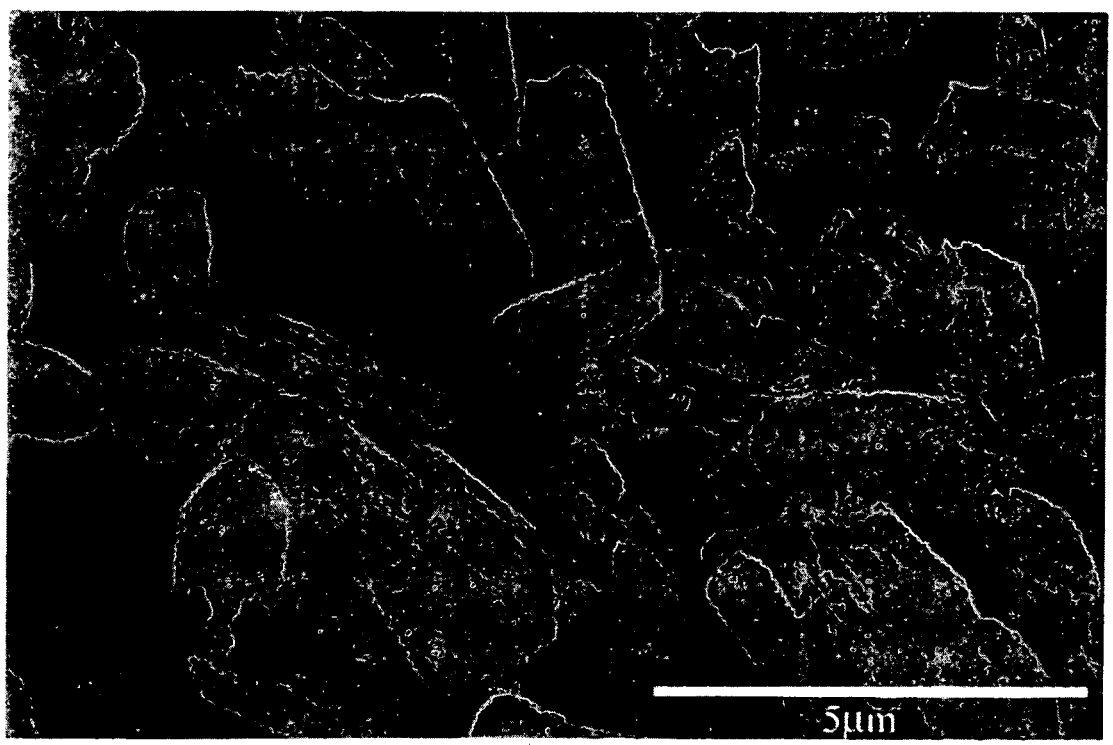
FIG. 5 is an SEM micrograph of catalyst sample 2E.
Figure 6:
FIG. 6 is an SEM micrograph of catalyst sample 3A.
Figure 7:
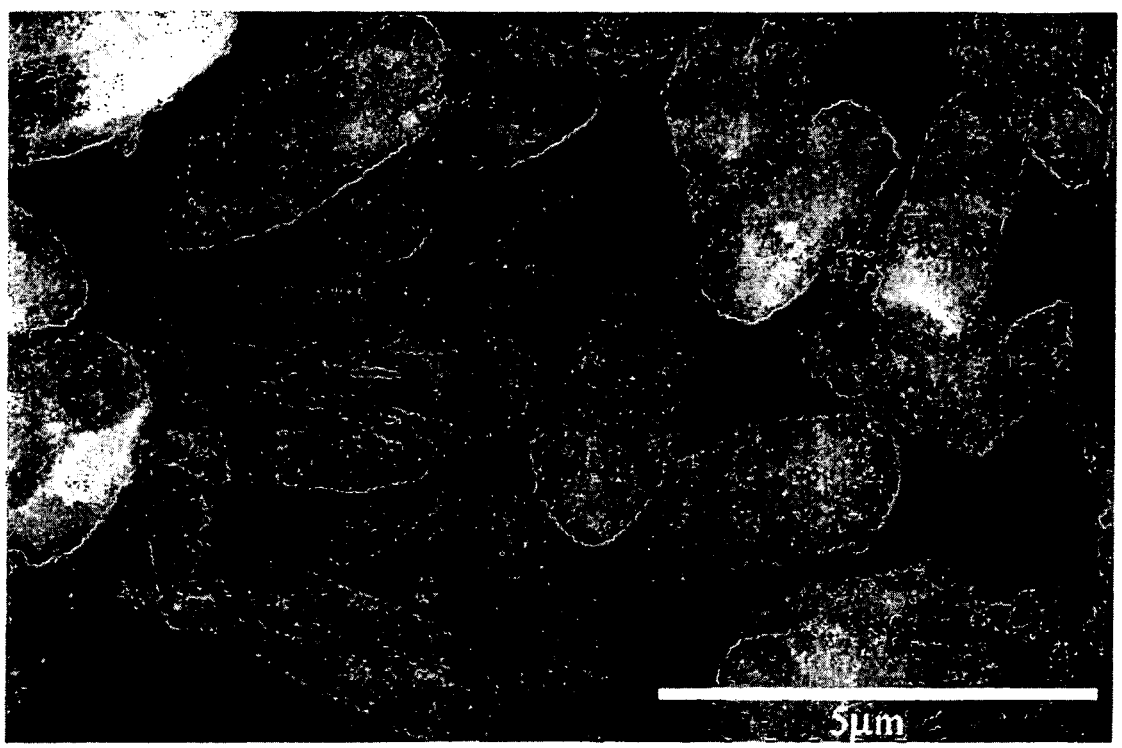
FIG. 7 is an SEM micrograph of catalyst sample 3B.
Figure 8:
FIG. 8 is an SEM micrograph of catalyst sample 3C.
Figure 9:
FIG. 9 is an SEM micrograph of catalyst sample 3D.
Figure 10:
FIG. 10 is an SEM micrograph of catalyst sample 3E.
Figure 11:
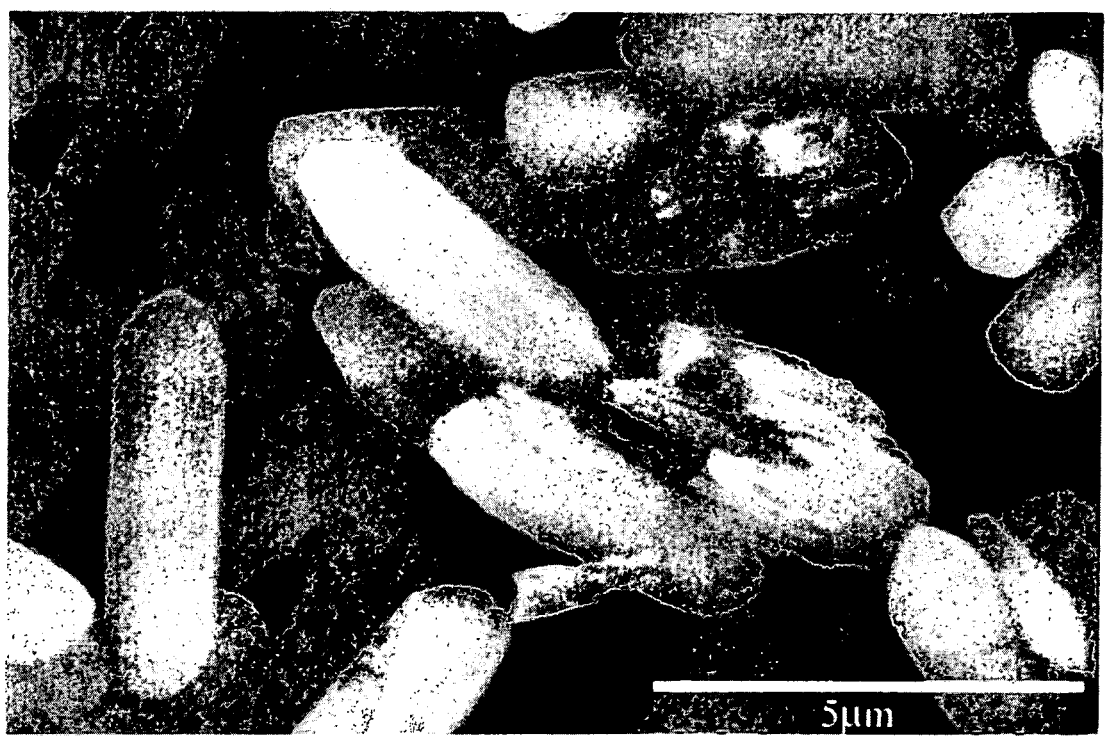
FIG. 11 is an SEM micrograph of catalyst sample 3F.
Figure 12:
FIG. 12 is an SEM micrograph of catalyst sample 3G.
Figure 13:
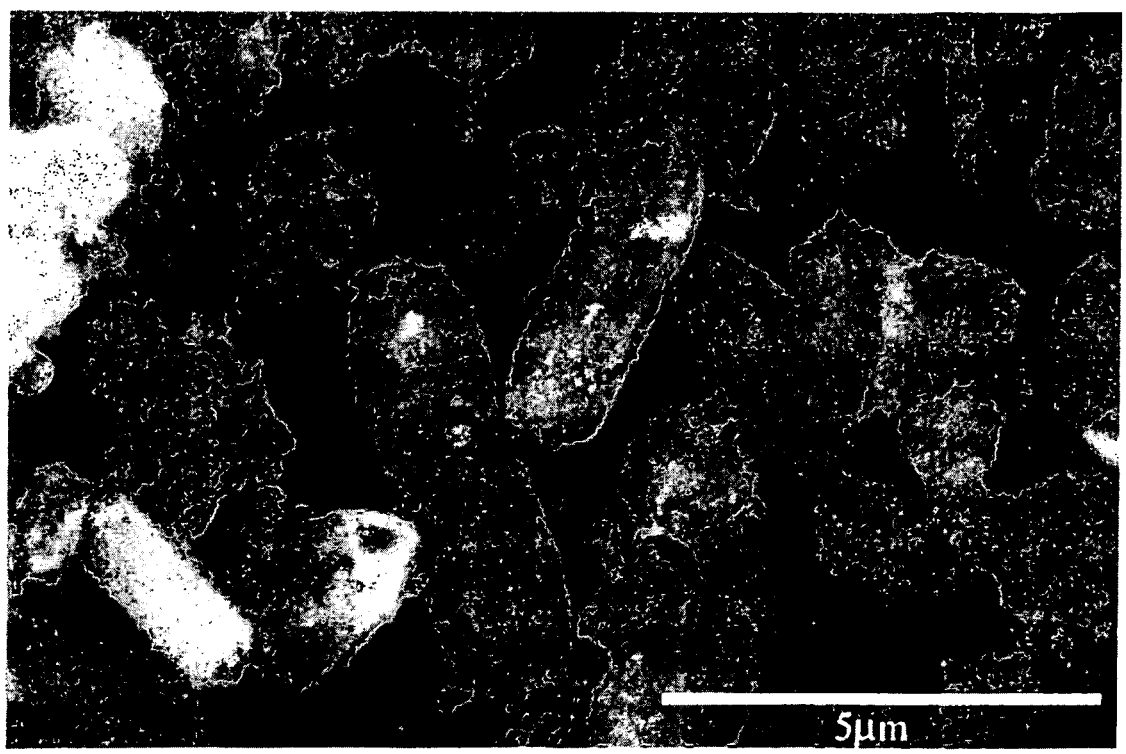
FIG. 13 is an SEM micrograph of catalyst sample 3H.
Figure 14:
FIG. 14 is an SEM micrograph of catalyst sample 3I.
Figure 15:
FIG. 15 is an SEM micrograph of catalyst sample 3J.
Figure 16:
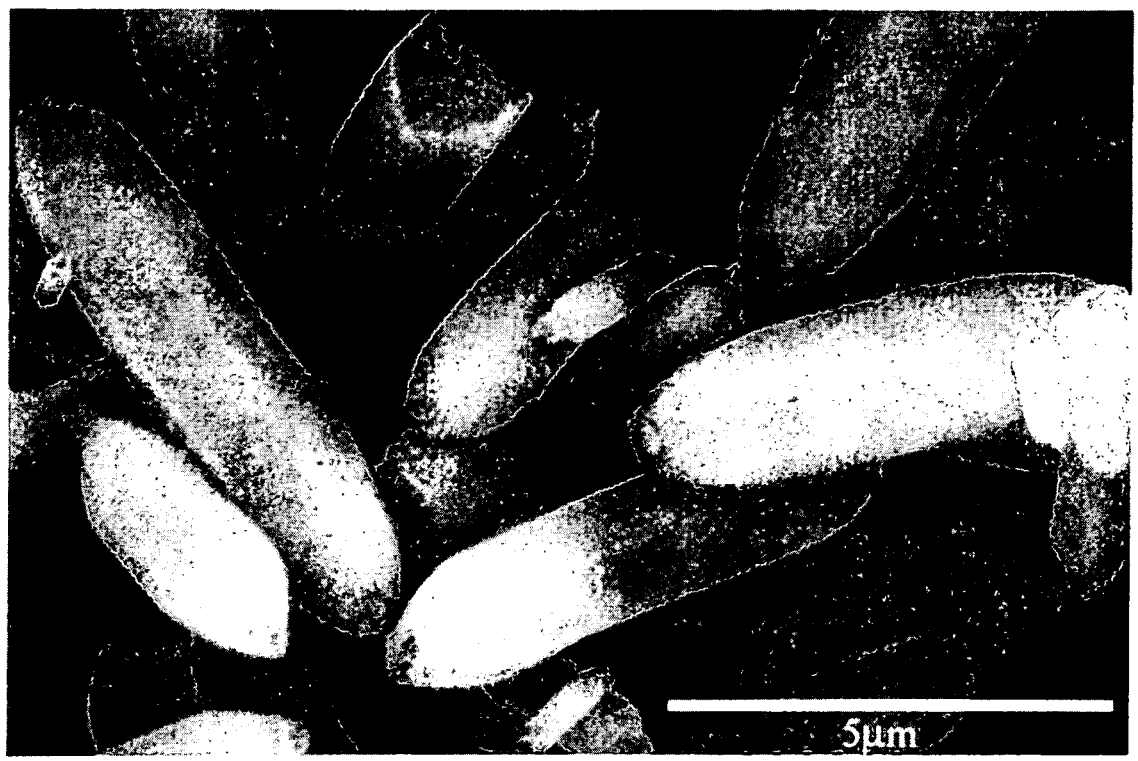
FIG. 16 is an SEM micrograph of catalyst sample 3K.

As mentioned above, this invention is drawn to a MgMxAPSO-31 molecular sieve having a particular crystalline structure wherein Mg represents framework magnesium and Mx represents a second framework element selected from one or more of the group consisting of manganese, cobalt, nickel, iron and zinc. The molecular sieve of the invention can be understood by reference to the disclosure of U.S. Pat. No. 4,758,419, relating to MgAPSO-31 molecular sieves and incorporated herein by reference thereto. MgMxAPSO sieves have a microporous crystalline framework structure of $MgO_2^{-2}$, $MxO_2^{-2}$, $AlO_2^{-}$, $PO_2^{+}$, and $SiO_2$ tetrahedral units having an empirical chemical composition on an anhydrous basis expressed by the formula:

$$mR:(Mg_vMx_wAl_xP_ySi_z)O_2$$

wherein "R" represents at least one organic templating agent present in the intracrystalline pore system; "m" represents the molar amount of "R" present per mole of $(Mg_vMx_wAl_xP_ySi_z)O_2$ and has a value of zero to about 0.3; and "v", "w", "x", "y" and "z" represent the mole fractions of element magnesium, second framework element, aluminum, phosphorus and silicon, respectively, present as tetrahedral oxides. The mole fraction of each framework constituent of the molecular sieve is defined as a compositional value which is plotted in a phase diagram analogous to that of U.S. Pat. No. 4,758,419. The mole fractions "v", "w", "x", "y" and "z" are generally defined as being within the limiting compositional values or points as follows:

| | Mole Fraction | | |
|---|---|---|---|
| Point | x | y | (z + y + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

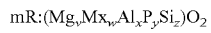

It is an essential aspect of the present invention that the content of each of the magnesium and the second element content of the MgMxAPSO-31 sieve is controlled within narrow limits. Specifically, each of the mole fraction "v" of framework magnesium and the mole fraction 'w' of the second element in the molecular sieves of the invention is between about 0.002 and about 0.01. The mole fraction in the sieve framework of magnesium preferably is between about 0.003 and 0.008 and the mole fraction of the second element Mx preferably is between about 0.002 and 0.008. Although the concentration of Mx may in some instances be lower, e.g., as low as about 0.0015 if other parameters of the sieve are within range, this is not a preferred concentration.

MgMxAPSO sieves generally are synthesized by hydrothermal crystallization from an aqueous reaction mixture containing reactive sources of magnesium, the second element, silicon, aluminum and phosphorus and an organic templating agent for an effective time at effective conditions of pressure and temperature.

The organic templating agent, if any, can be selected from among those disclosed in U.S. Pat. No. 4,758,419. Generally this agent will contain one or more elements selected from Group VA (IUPAC 15) of the Periodic Table [See Cotton and Wilkinson, Advanced Inorganic Chemistry, John Wiley & Sons (Sixth Edition, 1999)], preferably nitrogen or phosphorus and especially nitrogen, and at least one alkyl or aryl group having from 1 to 8 carbon atoms. Preferred compounds include the amines and the quaternary phosphonium and quaternary ammonium compounds. Mono-, di- and tri-amines are advantageously utilized, either alone or in combination with a quaternary ammonium compound. Especially preferred amines include di-isopropylamine, di-n-propylamine, triethylamine and ethylbutylamine.

The reaction source of silicon may be silica, either as a silica sol or as fumed silica, a reactive solid amorphous precipitated silica, silica gel, alkoxides of silicon, silicic acid or alkali metal silicate and mixtures thereof.

The most suitable reactive source of phosphorus yet found for the instant process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds selected as templating agents do not, apparently, serve as reactive sources of phosphorus, but these compounds may be transformed in situ to a reactive source of phosphorus under suitable process conditions.

The preferred aluminum source is either an aluminum alkoxide, such as aluminum isoproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive sources of magnesium and of one or more of manganese, cobalt, nickel, iron and/or zinc can be introduced into the reaction system in any form which permits the formation in situ of a reactive form of magnesium and the second element, i.e., reactive to form the framework tetrahedral unit $MgO_2^{-2}$. Compounds which may be employed include oxides, hydroxides, alkoxides, nitrates, sulfates, halides, carboxylates (e.g. acetates and the like), organo-metallics and mixtures thereof.

Crystallization generally is effected in a sealed pressure vessel, preferably lined with an inert plastic material such as polytetrafluoroethylene. While not essential in general to the synthesis of compositions of the invention, stirring or other moderate agitation of the reaction mixture and/or seeding the reaction mixture with seed crystals, e.g., of MgAPSO or of a topologically similar aluminophosphate, aluminosilicate or other molecular sieve composition, may facilitate the crystallization procedure. The reaction mixture is maintained advantageously under autogenous pressure at a temperature between 50° and 250° C., and preferably between 100° and 200° C., for a period of several hours to several weeks. The crystallization period advantageously will be between about 4 hours and 20 days. The MgMxAPSO-31 product is recovered by any convenient method such as centrifugation or filtration.

The criticality of crystallite size is believed to relate to the conversion of ethylbenzene in the isomerization process being diffusion-limited rather than surface-reaction limited, although such theory in not intended in any way to limit the invention. The critical dimensions of the crystallites of the invention may be realized in any manner which is effective to reduce and control crystallite size. Preferable methods include high-speed stirring during crystallization to achieve high mass-transfer rates, higher solids in the reaction mixture, control of temperature and residence time of the reactants, and use of suitable templates. Larger crystallites may be milled to obtain smaller sizes, although this method is not preferred due to the range of sizes effected and possible structural damage.

Optimally the MgMxAPSO-31 product comprises small crystallites, which favor high ethylbenzene conversion in a process isomerizing $C_8$ aromatics as demonstrated in the examples. Preferably the crystallites have a median diameter, measured by SEM, of less than about 2.5 micron. Median crystallite length along the direction of the pores of the sieve, designated the c-axis, is less than 4 micron.

After crystallization the MgMxAPSO-31 product may be isolated and advantageously washed with water and dried in air. The as-synthesized MgMxAPSO-31 will typically contain within its internal pore system at least one form of any templating agent, also referred to herein as the "organic moiety", employed in its formation. Most commonly the organic moiety is present, at least in part, as a charge-balancing cation. In some cases, the MgMxAPSO-31 pores are sufficiently large and the organic molecule sufficiently small that the removal of the latter may be effected by conventional desorption procedures. Generally, however, the organic moiety is an occluded molecular species which is too large to move freely through the pore system of the MgMxAPSO-31 product and must be thermally degraded and removed by calcining at temperatures of from 2000 to 700° C.

It is within the scope of the invention that a catalyst composite prepared from the MgMxAPSO-31 of the invention comprises one or more additional non-zeolitic molecular sieves. Preferably the non-zeolitic molecular sieves are as a multi-compositional, multi-phase composite having contiguous phases, a common crystalline framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. Suitable non-zeolitic molecular sieves include but are not limited to those of U.S. Pat. Nos. 4,440,871, 4,567,029 and 4,793,984, incorporated by reference.

A catalyst composite preferably is prepared by combining the molecular sieves of the invention with a binder for convenient formation of catalyst particles. The binder should be a porous, adsorptive support having a surface area of about 25 to about 500 m²/g, uniform in composition and relatively refractory to the conditions utilized in the hydrocarbon conversion process. The term "uniform in composition" denotes a support which is unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO$—$Al_2O_3$ where M is a metal having a valence of 2; and (6) combinations of materials from one or more of these groups.

The preferred matrices for use in the present invention are refractory inorganic oxides, with best results obtained with a binder comprising alumina. Suitable aluminas are the crystalline aluminas known as the gamma-, eta-, and theta-aluminas. Excellent results are obtained with a matrix of substantially pure gamma-alumina. In addition, in some embodiments, the alumina matrix may contain minor proportions of other well known refractory inorganic oxides such as silica, zirconia, magnesia, etc. Whichever type of matrix is employed, it may be activated prior to use by one or more treatments including but not limited to drying, calcination, and steaming.

Using techniques commonly known to those skilled in the art, the catalyst composite of the instant invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing.

A preferred form for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

An alternative shape of the composite is a sphere, continuously manufactured by the well-known oil drop method. Preferably, this method involves dropping the mixture of molecular sieve, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50°-200° C. and subjected to a calcination procedure at a temperature of about 450°-700° C. for a period of about 1 to about 20 hours. This treatment effects conversion of the hydrogel to the corresponding alumina matrix.

A preferred component of the present catalyst composite is a platinum-group metal including one or more of platinum, palladium, rhodium, ruthenium, osmium, and iridium. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. The platinum-group metal component generally comprises from about 0.01 to about 2 mass % of the final catalytic composite, calculated on an elemental basis.

The platinum-group metal component may be incorporated into the catalyst composite in any suitable manner. The preferred method of preparing the catalyst normally involves the utilization of a water-soluble, decomposable compound of a platinum-group metal to impregnate the calcined zeolite/binder composite. For example, the platinum-group metal component may be added to the calcined hydrogel by commingling the calcined composite with an aqueous solution of chloroplatinic or chloropalladic acid.

It is within the scope of the present invention that the catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art.

The catalyst composite of the present invention may contain a halogen component. The halogen component may be either fluorine, chlorine, bromine or iodine or mixtures thereof. Chlorine is the preferred halogen component. The halogen component is generally present in a combined state with the inorganic-oxide support. The halogen component is preferably well dispersed throughout the catalyst and may comprise from more than 0.2 to about 15 wt. %, calculated on an elemental basis, of the final catalyst. The halogen component may be incorporated in the catalyst composite in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and calcined at a temperature of from 400° to about 650° C. in an air atmosphere for a period of from about 0.1 to about 10 hours until the metallic compounds present are converted substantially to the oxide form. The optional halogen component may be adjusted by including a halogen or halogen-containing compound in the air atmosphere.

The resultant calcined composite may be subjected to a substantially water-free reduction step to insure a uniform and finely divided dispersion of the optional metallic components. Preferably, substantially pure and dry hydrogen (i.e., less than 20 vol. ppm $H_2O$) is used as the reducing agent in this step. The reducing agent contacts the catalyst at conditions, including a temperature of from about 200° to about 650° C. and for a period of from about 0.5 to about 10 hours, effective to reduce substantially all of the Group Vil metal component to the metallic state.

The resulting reduced catalytic composite may, in some cases, be beneficially subjected to a presulfiding operation designed to incorporate in the catalytic composite from about 0.05 to about 0.5 mass % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 600° C. or more. It is generally a good practice to perform this presulfiding step operation under substantially water-free conditions.

MgMxAPSO-31 sieves of the invention are useful for the conversion of hydrocarbons to obtain a converted product. The sieves preferably are utilized in combination with at least one inorganic-oxide matrix and one or more metals as described herein. A hydrocarbon feedstock is converted at hydrocarbon-conversion conditions including a pressure of about atmospheric to 200 atmospheres, temperatures of about 50° to 600° C., liquid hourly space velocities of from about 0.1 to 100 hr 1, and, if hydrogen is present, hydrogen-to-hydrocarbon molar ratios of from about 0.1 to 80. Hydrocarbon-conversion processes which could advantageously employ catalyst composites containing the MgMxAPSO-31 sieves of the invention include isomerization, reforming, dehydrocyclization, dehydrogenation, disproportionation, transalkylation, dealkylation, alkylation, polymerization, hydrocracking and catalytic cracking.

A particularly advantageous use for the MgMxAPSO-31 sieves of the invention is in the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example, ortho-xylene, meta-xylene, para-xylene, ethylbenzene, ethyltoluenes, trimethylbenzenes, diethylbenzenes, triethyl-benzenes, methylpropylbenzenes, ethylpropylbenzenes, diisopropylbenzenes, and mixtures thereof.

Isomerization of a $C_8$-aromatic mixture containing ethylbenzene and xylenes is a particularly preferred application of the MgMxAPSO-31 sieves of the invention. Generally such mixture will have an ethylbenzene content in the approximate range of 5 to 50 mass %, an ortho-xylene content in the approximate range of 0 to 35 mass %, a meta-xylene content in the approximate range of 20 to 95 mass % and a para-xylene content in the approximate range of 0 to 15 mass %. It is preferred that the aforementioned $C_8$ aromatics comprise a non-equilibrium mixture, i.e., at least one $C_8$-aromatic isomer is present in a concentration that differs substantially from the equilibrium concentration at isomerization conditions. Usually the non-equilibrium mixture is prepared by removal of para- and/or ortho-xylene from a fresh $C_8$ aromatic mixture obtained from an aromatics-production process.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated, but may be present in minor quantities in various streams. The process of this invention allows the isomerization of alkylaromatic-containing streams such as catalytic reformate with or without subsequent aromatics extraction to produce specified xylene isomers, particularly para-xylene. A $C_8$-aromatics feed to the present process may contain nonaromatic hydrocarbons, i.e., naphthenes and paraffins, in an amount up to 30 mass %.

According to the process of the present invention, an alkylaromatic hydrocarbon charge stock, preferably a non-equilibrium mixture of $C_8$ aromatics, and preferably in admixture with hydrogen, is contacted with a catalyst of the type hereinabove described in an alkylaromatic-hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the charge stock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic charge stock is contacted with the hereinbefore-described catalytic combination as in an isomerization zone while maintaining the zone at appropriate alkylaromatic-isomerization conditions. The conditions comprise a temperature ranging from about 0° to 600° C. or more, and preferably is in the range of from about 300° to 500° C. The pressure generally is from about 1 to 100 atmospheres absolute, preferably less than about 50 atmospheres. Sufficient catalyst is contained in the isomerization zone to provide a liquid hourly space velocity of charge stock of from about 0.1 to 30 hr$^{-1}$, and preferably 0.5 to 10 hr$^{-1}$. The hydrocarbon charge stock optimally is reacted in admixture with hydrogen at a hydrogen/hydrocarbon mole ratio of about 0.5:1 to about 25:1 or more. Other inert diluents such as nitrogen, argon and light hydrocarbons may be present, and water may be added to the charge stock in an amount of from about 1 to about 1000 mass-ppm (parts per million).

It is within the scope of the invention that the alkylaromatic-hydrocarbon charge stock is contacted with two or more catalysts in the alkylaromatic-hydrocarbon isomerization zone. In this system, a hydrogen-rich gas and the feed mixture are preheated by suitable heating means to the desired reaction temperature and then passed into an isomerization zone containing a fixed bed or beds of two or more catalysts. The isomerization zone may comprise a single reactor or two or more separate reactors with suitable means therebetween to ensure that the desired isomerization temperature is maintained at the entrance to each zone. The two or more catalysts thus may be contained in separate reactors, arranged sequentially in the same reactor, mixed physically, or composited as a single catalyst. Each reactor may contain a catalyst bed in either upward-, downward-, or radial-flow fashion, and the reactants may be in the liquid phase, a mixed liquid-vapor phase, or a vapor phase when contacted with each catalyst.

The two or more catalysts may comprise two catalysts of the present invention as described herein or one catalyst of the invention and one or more selected from the group consisting of other non-zeolitic molecular-sieves and zeolitic aluminosilicates. Preferably the catalysts are arranged in sequence, with the feed contacting a zeolitic-aluminosilicate catalyst in a first isomerization zone to isomerize xylenes and produce an intermediate stream which is contacted with the catalyst of the invention in a second isomerization zone at second isomerization conditions to isomerize ethylbenzene to increase the para-xylene content of the product to a higher-than-equilibrium concentration at second isomerization conditions. First and second isomerization conditions are within the limits of the conditions described above, except that first isomerization conditions may comprise the absence of hydrogen. Alternatively, the feed first contacts the catalyst of the present invention and then a zeolitic catalyst to obtain the isomerized product. Further details of an isomerization process comprising two or more catalysts are disclosed in U.S. Pat. No. 6,576,581 B1, incorporated herein by reference thereto.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

It is within the scope of the invention that the isomerized product contains a greater-than-equilibrium concentration of para-xylene, i.e., the ethylbenzene is converted selectively to para-xylene such that the content of para-xylene in the product exceeds that which would be obtained by conventional xylene isomerization. This effect can be obtained specifically in a two-catalyst process in which conventional xylene isomerization precedes isomerization using a catalyst of the present invention.

In a separation/isomerization process combination relating to the processing of an ethylbenzene/xylene mixture, a fresh $C_8$-aromatic feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

The following examples are presented for purpose of illustration only and are not intended to limit the scope of the present invention as presented in the claims.

EXAMPLES

The following examples are presented for purpose of illustration only and are not intended to limit the scope of the present invention. The examples illustrate the criticality of crystallite size and configuration and demonstrate the utility of the catalyst for isomerization of $C_8$ aromatics. These do not, however, limit the applicability of the present invention as described hereinabove.

Example 1

Six MgAPSO-31 samples of the known art were prepared to provide a base to illustrate the advantages of the invention. The gel composition in molar ratios during synthesis was $1P_2O_5:1Al_2O_3:xMgO:0.46SiO_2:1.8$ DPA:$50H_2O$ with x=0.015, 0.015, 0.022, 0.022, 0.030, 0.030. $H_3PO_4$ at a concentration of 50% was added to deionized water in a mixer operating at 650 RPM (revolutions per minute). An organic templating agent, dipropylamine (DPA), then was added and blended into the mixture. This was followed by Ludox AS-40 which was blended into the mixture. Magnesium acetate was then added to the mixture in an amount sufficient to achieve the proper concentrations in each sieve preparation, as shown below. Alumina in the form of aluminum tri-isopropoxide was added to the mixture gradually over a period of about 20 minutes and blended until the mixture was homogeneous. Finally, $AlPO_4$-31 seed was added and blended to achieve a homogeneous mixture. For each synthesis the total weight of the gel was 14,000 g. The resulting mixture was heated to about 185° C. at 500 RPM to effect crystallization at autogenous pressure. At the end of 3 hours the product was removed from the reaction vessel and centrifuged to recover solids which were washed three times with deionized water and dried at 100° C. for 24 hours. The dried solids then were extruded with 50 weight-% alumina binder to form trilobe particles and calcined at 600° C. The extrudates were then impregnated with 0.3 weight-% platinum, calcined and reduced at 566° C. and finally sulfided with $H_2S$. The resulting materials were as shown below, indicating magnesium, silicon, phosphorus and aluminum as a percentage of framework elements "T".

The materials prepared according to Example 1 were tested to demonstrate their effectiveness in converting ethylbenzene to xylenes. Tests were carried out using a pilot-plant flow reactor processing a $C_8$-aromatic feed comprising ethylbenzene and near-equilibrium xylenes (para-xylene/total xylenes of 0.23) having the following approximate composition in weight-%:

| | |
|---|---|
| Toluene | 1 |
| $C_8$ nonaromatics | 6 |
| Ethylbenzene | 14 |
| Total xylenes | 79 |

Testing conditions comprised a temperature of 350° C., pressure of 510 kPa, and 4 molar hydrogen to hydrocarbon ratio with space velocity adjusted to achieve 30% ethylbenzene conversion. Results were as follows in terms of required WHSV (weight hourly space velocity) and percent loss of $C_8$ ring ($C_8$ aromatics+naphthenic ring loss). The following procedures were used for calculating the various performance parameters:

$EB$ Conv, %=(($EB/C_8$ aromatics, % in feed)−($EB/C8$ aromatics, % in product)/($EB/C8$ aromatics, % in feed)

$PX/X$, %=($PX$ in product, %)/(Xylenes in product, %)

C8RL, %=(($C_8$ ring in feed, %)−($C_8$ ring in product, %))/($C_8$ ring in feed, %)

| | Mole % of Framework "T" and Performance | | | | | | |
|---|---|---|---|---|---|---|---|
| | 100Mg/T | 100Si/T | 100Al/T | 100P/T | WHSV | $C_8$RL, % | PX/X, % |
| Example 1A | 0.5 | 0.8 | 49.5 | 49.2 | 6.3 | 0.7 | 24.2 |
| Example 1B | 0.5 | 0.9 | 49.5 | 49.1 | 6.1 | 0.6 | 24.3 |
| Example 1C | 0.7 | 1.1 | 49.3 | 48.9 | 5.0 | 0.5 | 24.5 |
| Example 1D | 0.7 | 0.9 | 49.0 | 49.4 | 4.0 | 0.7 | 24.6 |
| Example 1E | 0.9 | 0.8 | 49.1 | 49.2 | 6.6 | 1.0 | 24.2 |
| Example 1F | 1.0 | 0.9 | 49.1 | 49.0 | 6.5 | 1.1 | 24.3 |

While magnesium is a critical element for determining the performance of MgAPSO-31 catalysts, the results of the pilot-plant tests for Example 1 indicate that, with the MgAPSO-31 catalysts of the known art, there is no performance benefit to be gained from increasing the amount of the divalent cation, here Mg, from 0.5% to 1.0%. In fact, at 1.0% Mg level, the C8RL is increased to an undesired level of 1.1%. Although catalyst activity is maintained at the higher sieve magnesium contents, such higher magnesium concentrations have a clearly adverse effect on $C_8$ ring loss with resulting lower product efficiency and higher operating costs.

Example 2

Four MgMxAPSO-31 samples of the invention were prepared wherein Mx was manganese or cobalt or nickel or iron, with at least 0.2% Mx (by mole based on T atoms), thus comprising MgMnAPSO-31, MgCoAPSO-31, MgNiAPSO-31 and MgFeAPSO-31 and compared to a MgAPSO-31 prepared according to prior art. These samples are identified as examples 2A-2E. The gel composition in molar ratios during synthesis for MgMxAPSO-31 samples were: $1P_2O_5:1Al_2O_3$:0.022MgO:0.011 MxO:0.46$SiO_2$:1.8DPA:$50H_2O$. The gel composition for MgAPSO-31 prior art was the same except for absence of Mx. The total amount of gel was 1,400 g in each case. In preparing the MgMxAPSO-31 or MgAPSO-31, $H_3PO_4$ at a concentration of 50% was added to deionized water in a mixer operating at 500 RPM (revolutions per minute). Then the organic templating agent, dipropylamine was added, followed by the divalent cation dissolved in water in the form of acetate. The next step was to add Ludox AS-40, followed by aluminum tri-isopropoxide and the $AlPO_4$-31 seeds and to achieve a homogeneous mixture. The resulting mixture was heated to about 185° C. at 500 RPM to effect crystallization at autogenous pressure for 3 hours. The product was removed from the reaction vessel and centrifuged to recover solids which were washed three times with deionized water and dried at 100° C. for 24 hours. The dried solids then were extruded with 50% alumina binder to form cylindrical particles and calcined at 575° C. Following this step the catalysts were impregnated with 0.3 wt-% platinum, calcined and reduced at 566° C. and sulfided with $H_2S$. The resulting materials are characterized below, indicating divalent cations, silicon, aluminum and phosphorus as a percentage of framework elements "T".

FIG. 1-5 are scanning electron micrographs (SEM) of catalyst samples 2A-2E prior to extrusion at 10 kV and a magnification of 10,000 times. The median crystal diameter and the median crystal length were 1.5 micron and 2.5 micron, respectively. These crystals were all very pitted, making the effective crystal diameter much smaller. In summary, the crystal morphology was very similar for examples 2A-2E, indicating that catalyst composition can be safely assumed to be the primary independent variable for these comparisons.

The materials prepared according to invention in Examples 2A-2D and the prior art material in Example 2E were tested to compare their effectiveness in converting ethylbenzene to xylenes. Tests were carried out using a pilot-plant flow reactor processing a $C_8$-aromatic feed comprising ethylbenzene and near-equilibrium xylenes (para-xylene/total xylenes of 0.23) having the composition described above in Example 1. Processing conditions comprised a temperature of 350° C., pressure of 450 kPa, and 4 molar hydrogen to hydrocarbon ratio with space velocity adjusted to achieve 30% ethylbenzene conversion. It is important to note here that, relative to Example 1, the lower pressure used for testing in Example 2 leads to lower activity relative to Example 1. However, since all tests in Example 2 were conducted at the same pressure, comparisons can be made among samples for which the pressure was the same. Results were as follows in terms of required WHSV (weight hourly space velocity) and percent loss of $C_8$-rings ($C_8$ ring loss or C8RL):

| Mole % of Framework "T" and Performance | | | | | | | |
|---|---|---|---|---|---|---|---|
| | Mg | Mx | Si | Al | P | WHSV | C8RL, % | PX/X, % |
| Example 2A | 0.6 | 0.2 Mn | 1.0 | 49.4 | 48.8 | 4.5 | 0.9 | 24.0 |
| Example 2B | 0.6 | 0.2 Fe | 1.1 | 49.4 | 48.7 | 4.6 | 0.7 | 24.2 |
| Example 2C | 0.6 | 0.2 Ni | 1.0 | 49.4 | 48.7 | 4.5 | 0.9 | 24.0 |
| Example 2D | 0.6 | 0.3 Co | 1.0 | 49.3 | 48.8 | 4.2 | 0.9 | 23.9 |
| Example 2E | 0.6 | | 1.1 | 49.4 | 48.9 | 3.5 | 0.8 | 24.2 |

Examples 2A-2D, samples prepared according to the invention showed higher activity than the prior art sample in Example 2E at comparable selectivities. These results indicate that when the divalent cation level in the molecular sieve was increased by introduction of a second divalent cation higher activity was achieved with little or no selectivity penalty, as observed from the C8RL and PX/X numbers.

Example 3

Eleven MgMxAPSO-31 samples not of the invention were prepared wherein Mx was either manganese or iron or nickel or cobalt. These samples were not of the invention either because of insufficient level of Mx (less than 0.2% by mole based on T atoms) and/or undesirable crystal morphology (median crystal diameter greater than or equal to 2.5 micron & crystal length greater than or equal to 4 micron). All eleven examples utilized the same gel composition during synthesis: $1P_2O_5$:$1Al_2O_3$:$0.022MgO$:$0.011$ $MxO$:$0.46SiO_2$:$1.8DPA$:$50H_2O$ (molar ratios). The total amount of gel was 1,400 g in each case.

For examples 3A-3D, first, $H_3PO_4$ at a concentration of 50% was added to deionized water in a mixer operating at 500 RPM. Then the acetate form of the divalent cations was dissolved in water and added to the gel, followed by the organic templating agent, dipropylamine. The next step was to add Ludox AS-40, followed by aluminum tri-isopropoxide and the $AlPO_4$-31 seeds and to achieve a homogeneous mixture. The resulting mixture was heated to about 185° C. at 500 RPM to effect crystallization at autogenous pressure for 3 hours. The product was removed from the reaction vessel and centrifuged to recover solids which were washed three times with deionized water and dried at 100° C. for 24 hours. The dried solids then were extruded with 50% alumina binder to form trilobe particles and calcined at 575° C. Following this step the catalysts were impregnated with 0.3 wt-% platinum, calcined and reduced at 566° C. and sulfided with $H_2S$. The resulting materials are characterized below, indicating divalent cations, silicon, aluminum and phosphorus as a percentage of framework elements "T".

For examples 3E-3H, first, $H_3PO_4$ at a concentration of 50% was added to deionized water in a mixer operating at 500 RPM. Then the organic templating agent, dipropylamine, was added to the gel. The next step was to add Ludox AS-40. This was followed by adding an aqueous solution of the acetate form of the divalent cations, then the aluminum tri-isopropoxide and the $AlPO_4$-31 seeds and to achieve a homogeneous mixture. The resulting mixture was heated to about 185° C. at 500 RPM to effect crystallization at autogenous pressure for 3 hours. The product was removed from the reaction vessel and centrifuged to recover solids which were washed three times with deionized water and dried at 100° C. for 24 hours. The dried solids then were extruded with 50% alumina binder to form trilobe particles and calcined at 575° C. Following this step the catalysts were impregnated with 0.3 wt-% platinum, calcined and reduced at 566° C. and sulfided with $H_2S$. The resulting materials are characterized below, indicating divalent cations, silicon, aluminum and phosphorus as a percentage of framework elements "T".

For examples 3I-3K, first, $H_3PO_4$ at a concentration of 50% was added to deionized water in a mixer operating at 500 RPM. Then the organic templating agent, dipropylamine, was added to the gel. The next step was to add Ludox AS-40. This was followed by adding the aluminum tri-isopropoxide, an aqueous solution of the acetate form of the divalent cations and the $AlPO_4$-31 seeds to achieve a homogeneous mixture. The resulting mixture was heated to about 185° C. at 500 RPM to effect crystallization at autogenous pressure for 3 hours. The product was removed from the reaction vessel and centrifuged to recover solids which were washed three times with deionized water and dried at 100° C. for 24 hours. The dried solids then were extruded with 50% alumina binder to form trilobe particles and calcined at 575° C. Following this step the catalysts were impregnated with 0.3 wt-% platinum, calcined and reduced at 566° C. and sulfided with $H_2S$. The resulting materials are characterized below, indicating divalent cations, silicon, aluminum and phosphorus as a percentage of framework elements "T".

FIG. 6-16 are scanning electron micrographs of catalyst examples 3A-3K prior to extrusion at 10 kV and a magnification of 10,000 times. The crystal diameter and/or the crystal length was much larger for catalyst examples 3A-3K not of the invention compared to examples 2A-2E prepared according to the invention.

The materials prepared according to Example 3 were tested to evaluate their effectiveness in converting ethylbenzene to xylenes. Tests were carried out using a pilot-plant flow reactor processing a C8-aromatic feed comprising ethylbenzene and near-equilibrium xylenes (para-xylene/total xylenes of 0.23) having the composition described above in Example 1. Processing conditions comprised a temperature of 350° C., pressure of 450 kPa, and 4 molar hydrogen to hydrocarbon ratio with space velocity adjusted to achieve 30% ethylbenzene conversion. Results were as follows in terms of required WHSV (weight hourly space velocity) and percent loss of C8A (C8 aromatics ring loss) (size representing diameter and length in microns):

Mole % of Framework "T", Crystal Diameter & Length (micron) and Performance

|  | Mg | Mx | Si | Al | P | Size | WHSV | C8RL, % | PX/X, % |
|---|---|---|---|---|---|---|---|---|---|
| Example 3A | 0.6 | 0.3 Mn | 1.0 | 49.4 | 48.9 | 2.5 & 5 | 2.5 | 0.8 | 24.4 |
| Example 3B | 0.7 | 0.1 Fe | 1.1 | 49.2 | 48.8 | 2.0 & 4 | 2.8 | 1.1 | 24.2 |
| Example 3C | 0.6 | 0.1 Ni | 1.0 | 49.4 | 48.9 | 2.5 & 6 | 3.5 | 1.3 | 24.2 |
| Example 3D | 0.6 | 0.3 Co | 0.8 | 49.4 | 48.9 | 2.5 & 5 | 4.3 | 0.9 | 24.0 |
| Example 3E | 0.6 | 0.2 Mn | 0.9 | 49.4 | 48.9 | 2.0 & 4 | 2.0 | 0.9 | 24.4 |
| Example 3F | 0.6 | 0.1 Fe | 1.0 | 49.4 | 48.9 | 1.5 & 4 | 2.8 | 1.1 | 24.2 |
| Example 3G | 0.6 | 0.2 Ni | 1.0 | 49.4 | 48.8 | 1.5 & 4 | 2.2 | 0.7 | 24.2 |
| Example 3H | 0.6 | 0.3 Co | 1.0 | 49.4 | 48.7 | 1.5 & 4 | 2.0 | 0.8 | 23.9 |
| Example 3I | 0.7 | 0.2 Mn | 1.0 | 49.3 | 48.8 | 2.5 & 5 | 3.4 | 1.4 | 24.2 |
| Example 3J | 0.7 | 0.1 Ni | 0.9 | 49.3 | 49.0 | 2.5 & 7 | 4.0 | 1.3 | 24.2 |
| Example 3K | 0.6 | 0.3 Co | 1.0 | 49.4 | 48.7 | 1.5 & 4 | 3.5 | 1.4 | 23.9 |

Figure 17:
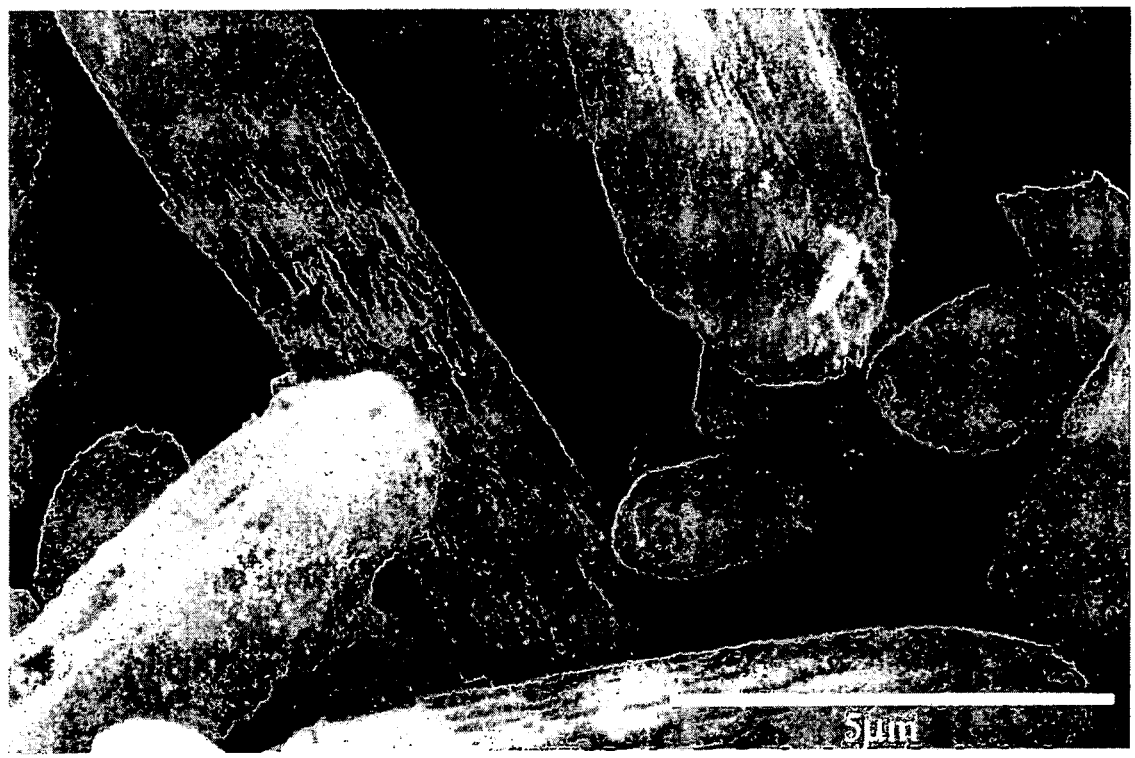
FIG. 17 is an SEM micrograph of catalyst sample 3L.

A prior art trilobe extrudate reference MgAPSO-31 example 3L with no Mx was prepared in order to compare to trilobe MgMxAPSO-31 examples 3A-3K not of the invention. Example 3L was prepared with a similar procedure to that used in examples 3A-3D and tested the same way. The scanning electron micrograph for example 3L catalyst was in FIG. 17. Also, based on the established relation between performance of cylindrical and trilobe extrudates the trilobe performance for prior art MgAPSO-31 example 2E was estimated and that is example 3M.

Mole % of Framework "T", Crystal Diameter & Length (micron) and Performance

|  | Mg | Mx | Si | Al | P | Size | WHSV | C8RL, % | PX/X, % |
|---|---|---|---|---|---|---|---|---|---|
| Example 3L | 0.6 | 0 | 1.6 | 49.4 | 48.4 | 2.5 & 5 | 4.8 | 1.0 | 24.3 |
| Example 3M | 0.6 | 0 | 1.1 | 49.4 | 48.9 | 1.5 & 2.5 | ~4.1 | ~1.7 | ~24.3 |

Comparison of the performances for MgMxAPSO-31 examples 3A-3K with prior art MgAPSO-31 examples 3L and 3M show no improvement in performance, verifying that examples 3A-3K were not prepared according to invention due to large crystal size and/or due to insufficient level of the second divalent cation.

Example 4

Figure 18:
FIG. 18 is an SEM micrograph of catalyst sample 4A.
Figure 19:
FIG. 19 is an SEM micrograph of catalyst sample 4B.

The catalyst preparation procedure that was used for examples 3A-3D was scaled up by a factor of ten and applied to MgAPSO-31 example 4A not of the invention and to MgMnAPSO-31 example 4B of the invention. The scanning electron micrographs for examples 4A and 4B are in FIGS. 18 and 19. For both examples the median crystal diameter was 0.5 micron and the median crystal length was 2 micron. This crystal size is much smaller than the crystal size obtained in examples 3A-3D, as would be expected from the faster tip speed achieved for the mixing blades in the larger size equipment during crystallization when the mixing rpm was kept the same as in the smaller scale example. Examples 4A and 4B catalysts were tested with the same procedure that was used for examples 3A-3D.

Mole % of Framework "T", Crystal Diameter & Length (micron) and Performance

|  | Mg | Mx | Si | Al | P | WHSV | C8RL, % | PX/X, % |
|---|---|---|---|---|---|---|---|---|
| Example 4A | 0.7 | 0 | 0.9 | 49.4 | 49.0 | 4.0 | 0.6 | 24.3 |
| Example 4B | 0.5 | 0.2 Mn | 1.2 | 48.8 | 49.3 | 4.9 | 0.7 | 24.4 |

Since the crystal morphology for examples 4A and 4B catalysts were essentially the same the higher activity obtained with example 4B is attributed to the presence of Mn, the second divalent cation. This set of examples again show that introduction of the second divalent cation helps increase activity with little or no selectivity penalty.

Example 5

Figure 20:
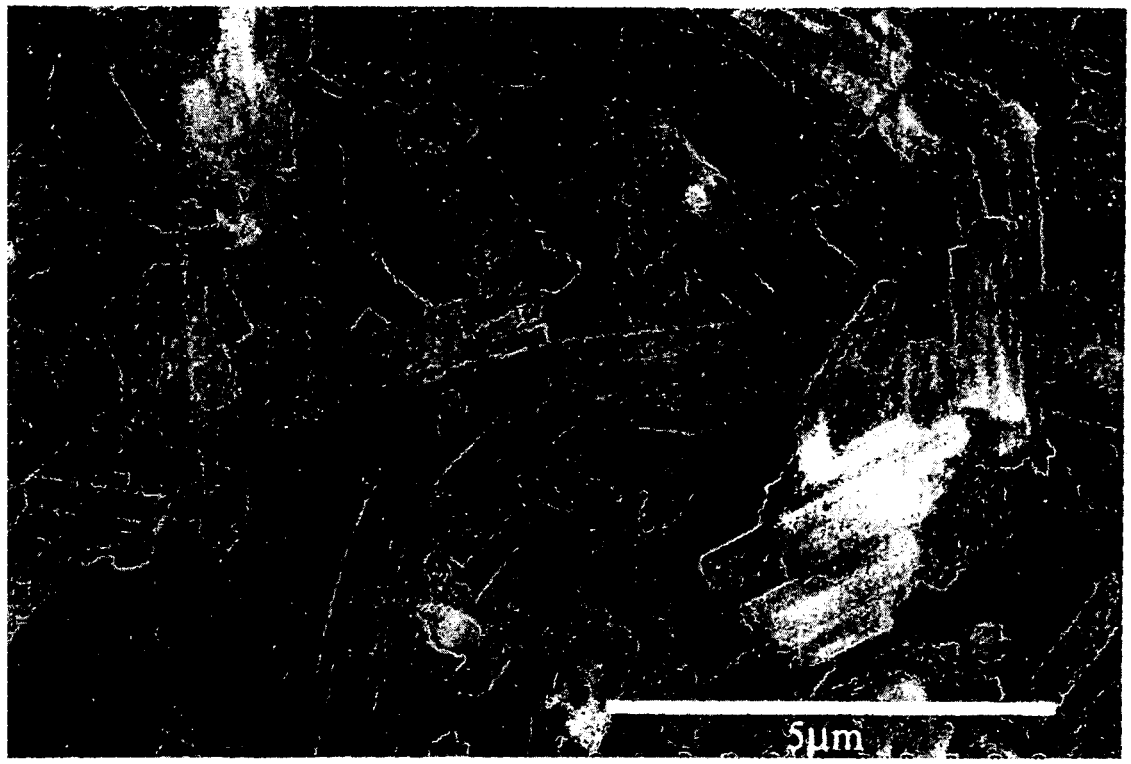
FIG. 20 is an SEM micrograph of catalyst sample 5A.
Figure 21:
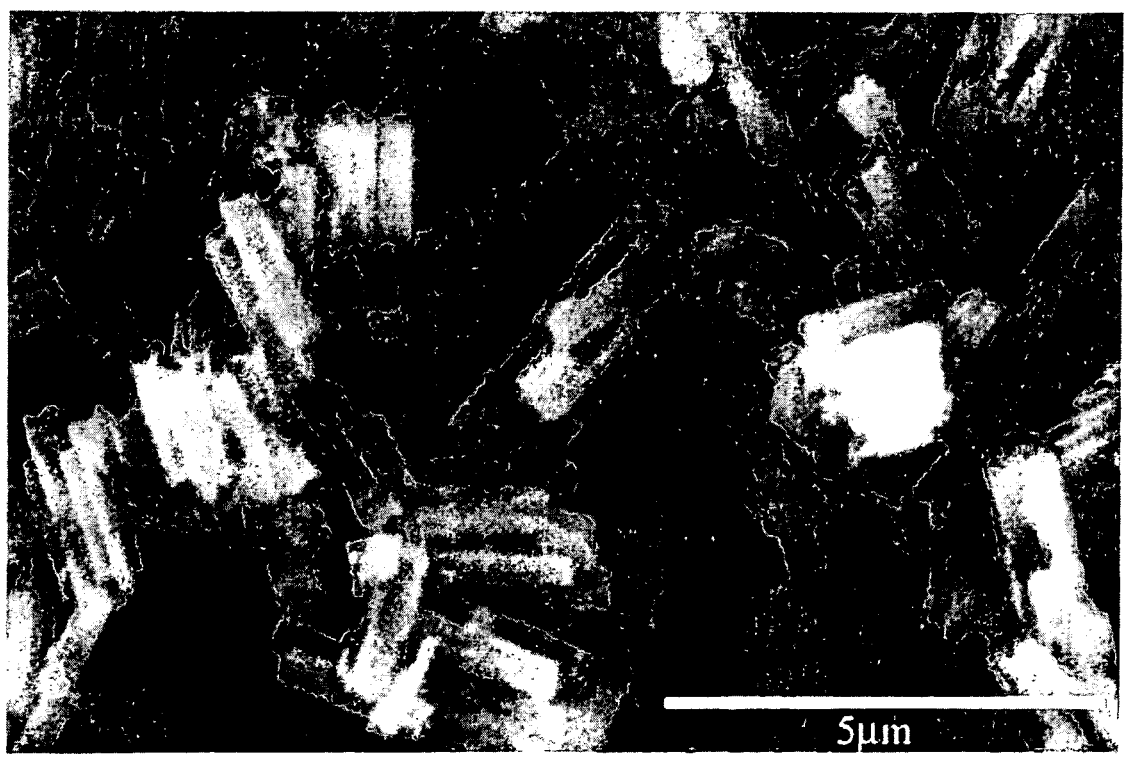
FIG. 21 is an SEM micrograph of catalyst sample 5B.

The catalyst preparation procedure that was used for examples 2A-2E was scaled up by a factor of ten and applied to MgAPSO-31 example 5A not of the invention and to MgMnAPSO-31 example 5B of the invention. The scanning electron micrographs for examples 5A and 5B are in FIGS. 20 and 21. For both examples the median crystal diameter was 0.5 micron and the median crystal length was 2 micron. This crystal size is much smaller than the crystal size obtained in examples 2A-2E, as would be expected from the faster tip speed achieved for the mixing blades in the larger size equipment during crystallization when the mixing rpm was kept the same as in the smaller scale example. Examples 5A and 5B catalysts were tested with the same procedure that was used for examples 2A-2E.

Mole % of Framework "T", Crystal Diameter & Length (micron) and Performance

|  | Mg | Mx | Si | Al | P | WHSV | C8RL, % | PX/X, % |
|---|---|---|---|---|---|---|---|---|
| Example 5A | 0.7 | 0 | 0.8 | 49.3 | 49.2 | 4.8 | 0.8 | 24.3 |
| Example 5B | 0.6 | 0.2 Mn | 0.8 | 49.3 | 49.1 | 5.7 | 0.7 | 24.3 |

Since the crystal morphology for examples 5A and 5B catalysts are essentially the same the higher activity obtained with example 5B is attributed to presence of Mn, the second divalent cation. Again this set of examples show that the introduction of the second divalent cation increases activity with little or nor selectivity penalty.

The invention claimed is:

1. A hydrocarbon-conversion process selected from isomerization, reforming, dehydrocyclization, dehydrogenation, disproportionation, transalkylation, dealkylation, polymerization, hydrocracking, and catalytic cracking, which comprises contacting a hydrocarbon feedstock in a conversion zone, at hydrocarbon-conversion conditions for isomerization, reforming, dehydrocyclization, dehydrogenation, disproportionation, transalkylation, dealkylation, polymerization, hydrocracking, and catalytic cracking, with a catalyst comprising a MgMxAPSO molecular sieve wherein Mg and Mx represent elements in the crystalline framework structure, Mg represents magnesium and Mx represents one or more of the group consisting of manganese, cobalt, nickel, iron and zinc, and wherein the molar proportion of each of Mg and Mx in the crystalline framework structure on an anhydrous basis is from about 0.002 to about 0.01 mol fraction, the sieve having a mean crystallite diameter of less than about 2.5 microns and a mean crystallite length of less than about 4 microns, to obtain a converted product, optionally a platinum-group metal component and optionally an inorganic-oxide matrix.

2. The process of claim 1 wherein the hydrocarbon-conversion process comprises an isomerization process, the hydrocarbon feedstock comprises a non-equilibrium feed mixture of xylenes and ethylbenzene, the conversion zone comprises an isomerization zone, the hydrocarbon-conversion conditions comprise isomerization conditions, and the converted product comprises $C_8$ aromatics having an increased content of para-xylene.

3. The process of claim 1 wherein the mole fraction in the sieve framework of magnesium is between about 0.003 and 0.008 and the mole fraction of the second element Mx is between about 0.002 and 0.008.

4. The process of claim 1 wherein the molar ratio of Mg to Mx is from about 0.2 to about 5.

5. The process of claim 1 wherein the MgMxAPSO molecular sieve consists essentially of MgMxAPSO-31.

6. The process of claim 1 wherein Mx consists essentially of manganese.

7. The process of claim 1 wherein Mx consists essentially of cobalt.

8. The process of claim 1 wherein Mx consists essentially of nickel.

9. The process of claim 1 wherein Mx consists essentially of iron.

10. The process of claim 1 wherein Mx consists essentially of zinc.

11. The process of claim 1 wherein the composite further comprises a platinum-group metal component.

12. The process of claim 11 wherein the platinum-group metal component comprises from about 0.1 to 5 mass % platinum on an elemental basis.

13. The process of claim 1 wherein the composition further comprises an inorganic-oxide matrix.

14. The process of claim 13 wherein the inorganic-oxide matrix comprises alumina.

15. An isomerization process which comprises contacting a non-equilibrium feed mixture of xylenes and ethylbenzene in an isomerization zone, at isomerization conditions, with a catalyst composite comprising a MgMxAPSO molecular sieve wherein Mg and Mx represent elements in the crystalline framework structure, Mg represents magnesium and Mx represents one or more of the group consisting of manganese, cobalt, nickel, iron and zinc, and wherein the molar proportion of each of Mg and Mx in the crystalline framework structure on an anhydrous basis is from about 0.002 to about 0.01 mol fraction, the sieve having a mean crystallite diameter of less than about 2.5 microns and a mean crystallite length of less than about 4 microns, a platinum-group metal component, and an inorganic-oxide matrix, to obtain a product comprising $C_8$ aromatics having an increased content of para-xylene.

16. An isomerization process which comprises the steps of:
   (a) contacting a non-equilibrium feed mixture of xylenes and ethylbenzene in a first isomerization zone, at first isomerization conditions, with a first isomerization catalyst comprising at least one zeolitic aluminosilicate and an inorganic-oxide binder, to obtain an intermediate stream; and:
   (b) contacting the intermediate stream in a second isomerization zone, at second isomerization conditions, with a second isomerization catalyst comprising a MgMxAPSO molecular sieve wherein Mg and Mx represent elements in the crystalline framework structure, Mg represents magnesium and Mx represents one or more of the group consisting of manganese, cobalt, nickel, iron and zinc, and wherein the molar proportion of each of Mg and Mx in the crystalline framework structure on an anhydrous basis is less than about 0.01 mol fraction, a platinum-group metal component, and an inorganic-oxide matrix, to obtain a product comprising $C_8$ aromatics having an increased content of para-xylene.

17. The process of claim 16 wherein the first isomerization conditions comprise the substantial absence of hydrogen.

18. The process of claim 16 further comprising addition of water to the charge stock in an amount of from about 1 to about 1000 mass-ppm.

19. The process of claim 16 wherein the increased content of para-xylene is higher than the equilibrium concentration at second isomerization conditions.

20. The process of claim 11 wherein the platinum-group metal component is in a reduced state.

* * * * *